(12) United States Patent
Gibson et al.

(10) Patent No.: US 9,273,011 B2
(45) Date of Patent: Mar. 1, 2016

(54) SUBSTITUTED PYRIDAZINES FOR THE TREATMENT OF PAIN

(71) Applicant: INHIBITAXIN LIMITED, Sandwich Kent (GB)

(72) Inventors: Karl Richard Gibson, Kent (GB); Dafydd Rhys Owen, Cambridge, MA (US)

(73) Assignee: Inhibitaxin Limited, Sandwich Kent, London ( * ) Notice: Subject to any disclaimer, the term of this patent is extended or adjusted under 35 U.S.C. 154(b) by 10 days.

(21) Appl. No.: 14/353,434

(22) PCT Filed: Oct. 26, 2012

(86) PCT No.: PCT/IB2012/055918
§ 371 (c)(1),
(2) Date: Apr. 22, 2014

(87) PCT Pub. No.: WO2013/061297
PCT Pub. Date: May 2, 2013

(65) Prior Publication Data
US 2014/0275100 A1    Sep. 18, 2014

Related U.S. Application Data

(60) Provisional application No. 61/552,651, filed on Oct. 28, 2011.

(51) Int. Cl.
| | |
|---|---|
| A61K 31/50 | (2006.01) |
| C07D 237/24 | (2006.01) |
| C07D 403/12 | (2006.01) |
| C07D 237/20 | (2006.01) |
| C07D 413/12 | (2006.01) |
| A61K 31/501 | (2006.01) |
| C07D 401/14 | (2006.01) |
| C07D 413/14 | (2006.01) |

(52) U.S. Cl.
CPC .............. *C07D 237/24* (2013.01); *A61K 31/50* (2013.01); *A61K 31/501* (2013.01); *C07D 237/20* (2013.01); *C07D 401/14* (2013.01); *C07D 403/12* (2013.01); *C07D 413/12* (2013.01); *C07D 413/14* (2013.01)

(58) Field of Classification Search
CPC .............................. A61K 31/50; C07D 237/24
USPC ........................................... 514/247; 544/224
See application file for complete search history.

(56) References Cited

U.S. PATENT DOCUMENTS

2009/0143385 A1    6/2009  Buettelmann et al.

FOREIGN PATENT DOCUMENTS

| WO | 2006034341 A2 | 3/2006 |
| WO | 2007127375 A2 | 11/2007 |
| WO | 2008123469 A1 | 10/2008 |
| WO | 2011133882 A1 | 10/2011 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
International Search Report and Written Opinion in PCT/IB2012/055918.

* cited by examiner

*Primary Examiner* — Douglas M Willis
(74) *Attorney, Agent, or Firm* — Dennis A. Bennett

(57) ABSTRACT

The invention provides compounds of formula I, (I) wherein: R represents a cyclic group selected from phenyl, heteroaryl, heterocyclyl and C 3-6 cycloalkyl; 10 wherein each cyclic group is optionally substituted with from 1 to 3 substituents selected from halo, C -6 alkyl optionally substituted with 1-3 halogen atoms, phenyl, C -6 alkoxy optionally substituted with 1-3 halogen atoms, cyano, heteroaryl 1a and heterocyclyl 1a; and wherein each cyclic group is optionally fused to a benzene ring or a 5- or 16-membered heteroaromatic or heterocyclic ring each containing from 1 to 3 heteroatoms (selected from N, O and S); and when the group is substituted the substitution may occur anywhere on the optionally fused ring system as a whole; and wherein heterocyclyl and heterocyclyl 1a may additionally be substituted with =O; 20 X represents a bond or C -6 alkylene (which may be straight or branched); R 2 represents H or C -6 alkyl; R 3 represents H or C -6 alkyl; Y represents a bond or C -6 alkylene (which may be straight or branched, and optionally substituted with OH or CF 3); 2 R 4 represents a cyclic group selected from phenyl, heteroaryl 4, heterocyclyl 4 and C 3-6 cycloalkyl; wherein each cyclic group is optionally substituted with from 1 to 3 substituents selected from halo, C -6 alkyl optionally substituted with 1-3 halogen atoms, TET01063WO 4 phenyl, C -6 alkyl substituted with phenyl, C -6 alkoxy optionally substituted with -3 halogen atoms, cyano, heteroaryl 4a and heterocyclyl 4a; and wherein each cyclic group is optionally fused to benzene ring or a 5- or 6-membered heteroaromatic or heterocyclic ring each containing from 1 to 3 heteroatoms (selected from N, O and S); and when the group is substituted the substitution may occur anywhere on the optionally fused ring system as a whole; and wherein heterocyclyl 4 and heterocyclyl 4a may additionally be substituted with =O; heteroaryl, heteroaryl 1a, heteroaryl 4 and heteroaryl 4a independently represent a 5- or 6-membered heteroaryl group containing from 1 to 3 heteroatoms (selected from N, O and 10 S); and heterocyclyl, heterocyclyl 1a, heterocyclyl 4 and heterocyclyl 4a independently represent a 5- or 6-membered heterocyclyl group containing from 1 to 3 heteroatoms (selected from N, O and S); and pharmaceutically acceptable salts and solvates thereof. 1 The compounds are useful as pharmaceuticals, particularly in the treatment of fibrotic diseases, cancer and pain.

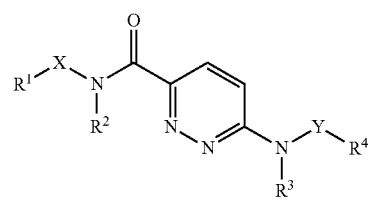

(I)

20 Claims, No Drawings

SUBSTITUTED PYRIDAZINES FOR THE TREATMENT OF PAIN

CROSS REFERENCE TO RELATED APPLICATIONS

This application is a U.S. national stage filing under 35 U.S.C. §371 of PCT International Application No. PCT/IB2012/055918, filed Oct. 26, 2012, which claims the benefit of priority of US Application Serial No. 61/552,651 filed Oct. 28, 2011. Each of the above-referenced applications is expressly incorporated by reference herein its entirety.

This invention relates to pyridazine derivatives useful in therapy, to processes for the preparation of such derivatives, to compositions containing such derivatives, and to the uses of such derivatives.

The pyridazine derivatives of the present invention have a number of therapeutic applications, particularly in the treatment of pain. This is believed to result from them being inhibitors of the enzyme autotaxin.

Autotaxin (ATX) is a member of the family of nucleotide pyrophosphatases/phosphodiesterases (NPP1-7) and is also referred to as NPP2 [Stefan et al, "NPP-type ectophosphodiesterases: unity in diversity," *Trends in Biochemical Sciences*, vol. 30, no. 10, pp. 542-550, 2005]. It is a glycoprotein with four possible N-glycosylation sites, synthesized as a pre-proenzyme and is secreted to extracellular space following two N-terminal cleavages (27 and 8 amino acids) [Stracke et al, "Autotaxin is an N-linked glycoprotein but the sugar moieties are not needed for its stimulation of cellular motility," *Melanoma Research*, vol. 5, no. 4, pp. 203-209, 1995; Jansen et al, "Proteolytic maturation and activation of autotaxin (NPP2), a secreted metastasis-enhancing lysophospholipase D," *Journal of Cell Science*, vol. 118, no. 14, pp. 3081-3089, 2005].

ATX is a constitutively active enzyme possessing activity of phospholipase D. It hydrolyzes the head groups of lysophospho lipids (LPC) to lysophosphatidic acid (1 or 2-acyl-sn-glycerol-3-phosphate, LPA) and also acts on sphingosylphosphorylcholine to produce sphingosine 1-phosphate (S1P) [Yuelling et al, "Autotaxin (ATX): a multi-functional and multi-modular protein possessing enzymatic lysoPLD activity and matricellular properties," *Biochimica et Biophysica Acta*, vol. 1781, no. 9, pp. 525-530, 2008; Nakanaga et al, "Autotaxin—An LPA producing enzyme with diverse functions," *Journal of Bio chemistry*, vol. 148, no. 1, pp. 13-24, 2010]. Both LPA and S1P are strong inhibitors of ATX with affinity to enzyme approximately 1000-fold higher than reported for ATX substrates [Van Meeteren et al, "Inhibition of autotaxin by lysophosphatidic acid and sphingosine 1-phosphate," *Journal of Biological Chemistry*, vol. 280, no. 22, pp. 21155-21161, 2005].

The expression of Autotaxin has been detected in brain, ovary, lung, intestine, and kidney. Autotaxin protein has been detected in blood, cerebrospinal, seminal fluid, urine and saliva [Sugiura et al, "Lysophosphatidic acid, a growth factor-like lipid, in the saliva," *Journal of Lipid Research*, vol. 43, no. 12, pp. 2049-2055, 2002; Tanaka et al, "Prostatic acid phosphatase degrades lysophosphatidic acid in seminal plasma," *FEBS Letters*, vol. 571, no. 1-3, pp. 197-204, 2004; Masuda et al, "Serum autotaxin measurement in haematological malignancies: a promising marker for follicular lymphoma," *British Journal of Haematology*, vol. 143, no. 1, pp. 60-70, 2008; Nakamura et al, "Analysis of serum and urinary lysophospholipase D/autotaxin in nephrotic syndrome," *Clinical Chemistry and Laboratory Medicine*, vol. 46, no. 1, pp. 150-151, 2008; Nakamura et al, "Autotaxin enzyme immunoassay in human cerebrospinal fluid samples," *Clinica Chimica Acta*, vol. 405, no. 1-2, pp. 160-162, 2009].

ATX is the main source of blood LPA (~0.1 µM plasma and ~1 µM serum), but not S1P [Tanaka et al, "Autotaxin stabilizes blood vessels and is required for embryonic vasculature by producing lysophosphatidic acid," *Journal of Biological Chemistry*, vol. 281, no. 35, pp. 25822-25830, 2006; Alvarez et al, "Autocrine and paracrine roles of sphingosine-1-phosphate," *Trends in Endocrinology and Metabolism*, vol. 18, no. 8, pp. 300-307, 2007]. In addition to LPC and sphingosylphosphorylcholine, ATX hydrolyzes ATP: however, the affinity to ATP is at least 50-fold lower than for lysophospholipids [Gijsbers et al, "The hydrolysis of lysophospholipids and nucleotides by autotaxin (NPP2) involves a single catalytic site," *FEBS Letters*, vol. 538, no. 1-3, pp. 60-64, 2003; Van Meeteren et al, "Regulation and biological activities of the autotaxin-LPA axis," *Progress in Lipid Research*, vol. 46, no. 2, pp. 145-160, 2007].

The major product of ATX, LPA acts on target cells through specific G-protein-coupled receptors (LPA1/Edg2, LPA2/Edg4, LPA3/Edg7, LPA4/GPR23/P2Y9, LPA5/GPR92, LPA6/P2Y5). LPA receptors are broadly expressed throughout the body (neuronal, peripheral and central; platelets) and are up-regulated in pathological conditions including, for example, fibrosis (renal, liver, lung), cancer (overian and breast), and osteoarthritis [Aoki et al, "Two pathways for lysophosphatidic acid production," *Biochimica et Biophysica Acta*, vol. 1781, no. 9, pp. 513-518, 2008; Okudaira et al, "Biological roles of lysophosphatidic acid signaling through its production by autotaxin," *Biochimie*, vol. 92, no. 6, pp. 698-706, 2010]. The wide distribution of LPA receptors and the corresponding increase in ATX expression in disease makes ATX an excellent drug target for the treatment of a number of pathologies including fibrosis (eg renal, lung, and liver), cancer (including ovarian cancer, prostate cancer and breast cancer), pain, osteoarthritis, rheumatoid arthritis, multiple sclerosis, atherosclerosis, thrombosis, psoriasis, diabetic neuropathy, neuropathies and inflammatory conditions. Consequently, selective ATX inhibitors have the potential to treat a variety of diseases that involve the LPC/LPA ATX pathway.

The pyridazine derivatives of the present invention are potentially useful in the treatment of a wide range of disorders, particularly pain, acute pain, chronic pain, neuropathic pain, inflammatory pain, osteoarthritis, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain. Other conditions that may be treated with the pyridazine derivatives of the present invention include cancer (including ovarian cancer, prostate cancer and breast cancer), atherosclerosis, thrombosis, psoriasis, multiple sclerosis, fibrotic diseases including pulmonary fibrosis, Cirrhosis, endomyocardial fibrosis, mediastinal fibrosis, myelofibrosis, retroperitoneal fibrosis, nephrogenic systemic fibrosis, Crohn's disease, Keloid, old myocardial infarction, scleroderma/systemic sclerosis, atherofibrosis and adhesive capsulitis, neurodegenerative disorders, irritable bowel syndrome, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, causalgia, and conditions of lower urinary tract dysfunction.

There is a need to provide new ATX inhibitors that are good drug candidates. In particular, preferred compounds should bind potently to the ATX enzyme whilst showing little affinity for other receptors and enzymes which could give rise to unwanted side-effects, and should show functional activity as ATX inhibitors. They should be well absorbed from the gastrointestinal tract, be metabolically stable and possess favourable pharmacokinetic properties. They should be non-toxic and demonstrate few side-effects. Furthermore, the ideal drug candidate will exist in a physical form that is stable, non-hygroscopic and easily formulated.

The invention therefore provides a compound of formula I,

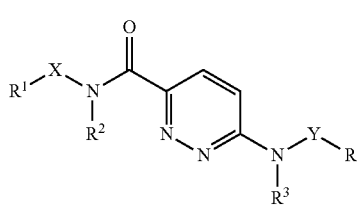

(I)

wherein:
$R^1$ represents a cyclic group selected from phenyl, heteroaryl$^1$, heterocyclyl$^1$ and $C_{3-6}$ cycloalkyl;
  wherein each cyclic group is optionally substituted with from 1 to 3 substituents selected from halo, $C_{1-6}$ alkyl optionally substituted with 1-3 halogen atoms, phenyl, $C_{1-6}$ alkoxy optionally substituted with 1-3 halogen atoms, cyano, heteroaryl$^{1a}$ and heterocyclyl$^{1a}$;
  and wherein each cyclic group is optionally fused to a benzene ring or a 5- or 6-membered heteroaromatic or heterocyclic ring each containing from 1 to 3 heteroatoms (selected from N, O and S); and when the group is substituted the substitution may occur anywhere on the optionally fused ring system as a whole; and wherein heterocyclyl$^1$ and heterocyclyl$^{1a}$ may additionally be substituted with =O;
X represents a bond or $C_{1-6}$ alkylene (which may be straight or branched);
$R^2$ represents H or $C_{1-6}$ alkyl;
$R^3$ represents H or $C_{1-6}$ alkyl;
Y represents a bond or $C_{1-6}$ alkylene (which may be straight or branched, and optionally substituted with OH or $CF_3$);
$R^4$ represents a cyclic group selected from phenyl, heteroaryl$^4$, heterocyclyl$^4$ and $C_{3-6}$ cycloalkyl;
  wherein each cyclic group is optionally substituted with from 1 to 3 substituents selected from halo, $C_{1-6}$ alkyl optionally substituted with 1-3 halogen atoms, phenyl, $C_{1-6}$ alkyl substituted with phenyl, $C_{1-6}$ alkoxy optionally substituted with 1-3 halogen atoms, cyano, heteroaryl$^{4a}$ and heterocyclyl$^{4a}$;
  and wherein each cyclic group is optionally fused to benzene ring or a 5- or 6-membered heteroaromatic or heterocyclic ring each containing from 1 to 3 heteroatoms (selected from N, O and S); and when the group is substituted the substitution may occur anywhere on the optionally fused ring system as a whole; and wherein heterocyclyl$^4$ and heterocyclyl$^{4a}$ may additionally be substituted with =O;
heteroaryl$^1$, heteroaryl$^{1a}$, heteroaryl$^4$ and heteroaryl$^{4a}$ independently represent a 5- or 6-membered heteroaryl group containing from 1 to 3 heteroatoms (selected from N, O and S); and
heterocyclyl$^1$, heterocyclyl$^{1a}$, heterocyclyl$^4$ and heterocyclyl$^{4a}$ independently represent a 5- or 6-membered heterocyclyl group containing from 1 to 3 heteroatoms (selected from N, O and S);
and pharmaceutically acceptable salts and solvates thereof (also referred to herein as "the compounds of the invention").

In the above definitions, halo means fluoro, chloro, bromo or iodo. Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene. Examples of cycloalkyl include cyclopropyl, cyclobutyl, cyclopentyl, cyclohexyl and cycloheptyl.

"Heteroaryl" is a radical formed from a heteroaromatic ring, for example thienyl, furanyl, pyridinyl, pyrrolyl, pyrazolyl, imidazolyl, oxazolyl, isoxazolyl, thiazolyl, isothiazolyl, triazolyl, oxadiazolyl, thiadiazolyl and tetrazolyl. Specific heteroaryl groups of interest include pyridinyl, pyrazolyl, imidazolyl and isoxazolyl.

"Heterocyclyl" is a radical formed from a saturated or partially saturated heterocyclic ring, for example tetrahydrofuranyl, tetrahydrothiophenyl, pyrrolidinyl, tetrahydropyranyl, piperazinyl and imidazolidinyl. Specific heterocyclyl groups of interest include pyrrolidinyl, imidazolidinyl and 2-oxoimidazolidinyl (imidazolidinyl substituted with =O).

Preferably $R^1$ represents a cyclic group selected from phenyl, heteroaryl$^1$ and heterocyclyl$^1$;
  wherein each cyclic group is optionally substituted with from 1 to 3 substituents selected from halo, $C_{1-6}$ alkyl optionally substituted with 1-3 halogen atoms, phenyl, $C_{1-6}$ alkoxy optionally substituted with 1-3 halogen atoms, cyano, heteroaryl$^{1a}$ and heterocyclyl$^{1a}$;
  and wherein each cyclic group is optionally fused to a benzene ring or a 5- or 6-membered heteroaromatic or heterocyclic ring each containing from 1 to 3 heteroatoms (selected from N, O and S); and when the group is substituted the substitution may occur anywhere on the optionally fused ring system as a whole; and wherein heterocyclyl$^1$ and heterocyclyl$^{1a}$ may additionally be substituted with =O;

More preferably $R^1$ is selected from difluorophenyl, 3,4-dimethylisoxazol-5-yl, N-(1-methyl-3-phenyl-1H-pyrazol-5-yl), 2-(2-oxoimidazolidin-1-yl, 1,3-dimethyl-1H-pyrazol-5-yl and imidazolyl $R^1$ represents phenyl substituted by one or two fluorine atoms, and pharmaceutically acceptable salts and solvates thereof;

Preferably X is selected from $CH_2$, a bond, $C_2H_4$ and $C_4H_8$
More preferably X is $CH_2$ or a bond.
Preferably $R^2$ is H, and pharmaceutically acceptable salts and solvates thereof;
Preferably $R^3$ is selected from H and C3H7.
More preferably $R^3$ is H.
Preferably Y is selected from $CH_2$, $CH(CH_2CH_2OH)$, $C_2H_4$ and a direct bond
More preferably Y is $CH_2$ or $CH(CH_2CH_2OH)$.
Preferably $R^4$ is selected from phenyl, heteroaryl$^4$ and heterocyclyl$^4$
More preferably $R^4$ is selected from methoxyphenyl, chlorophenyl, pyridinyl, 2,3-dihydro-1H-indenyl, dichlorophenyl, 2,6-difluoro-3-methyl phenyl, naphthyl, benzopyrrolidinyl and 5-methyl-3-phenyl-isoxazol-4-yl Most preferably $R^4$ is selected from methoxyphenyl, chlorophenyl, dichlorophenyl and 2,6-difluoro-3-methyl phenyl. s The various preferred embodiments of $R^1$, X, $R^2$, $R^3$, Y and $R^4$ should not be read in isolation; particularly preferred compounds of the invention will embody preferred moieties from one or more of the lists of preferred embodiments described.

Pharmaceutically acceptable salts of the compounds of formula I include the acid addition and base salts thereof.

Particularly preferred compounds of the present invention include:
1. N-(2,5-difluorobenzyl)-6-{[3-hydroxy-1-(4-methoxyphenyl)propyl]amino}pyridazine-3-carboxamide
2. N-(3,5-difluorobenzyl)-6-{[3-hydroxy-1-(4-methoxyphenyl)propyl]amino}pyridazine-3-carboxamide
3. 6-{[1-(4-chlorobenzyl)-2-hydroxyethyl]amino}-N-(3,4-dimethylisoxazol-5-yl)pyridazine-3-carboxamide
4. 6-[ethyl(pyridin-4-ylmethyl)amino]-N-(1-methyl-3-phenyl-1H-pyrazol-5-yl)pyridazine-3-carboxamide
5. N-(3,4-dimethylisoxazol-5-yl)-6-{[3-hydroxy-1-(4-methoxyphenyl)propyl]amino}pyridazine-3-carboxamide
6. 6-(2,3-dihydro-1H-inden-2-ylamino)-N-[2-(2-oxoimidazolidin-1-yl)ethyl]pyridazine-3-carboxamide
7. 6-[(3,5-dichlorobenzyl)amino]-N-[3-(1H-imidazol-1-yl)propyl]pyridazine-3-carboxamide
8. 6-{[1-(4-chlorophenyl)ethyl]amino}-N-(3,4-dimethylisoxazol-5-yl)pyridazine-3-carboxamide
9. 6-[(2,6-difluoro-3-methylbenzyl)amino]-N-(3,4-dimethylisoxazol-5-yl)pyridazine-3-carboxamide
10. N-(3,4-dimethylisoxazol-5-yl)-6-[(1-naphthylmethyl)amino]pyridazine-3-carboxamide
11. 6-[(2,3-dichlorobenzyl)amino]-N-(3,4-dimethyl-isoxazol-5-yl)pyridazine-3-carboxamide
12. 6-[(1-benzylpyrrolidin-3-yl)amino]-N-(3,4-dimethyl-isoxazol-5-yl)pyridazine-3-carboxamide
13. 6-{[1-(4-chlorobenzyl)-2-hydroxyethyl]amino}-N-(1,3-dimethyl-1H-pyrazol-5-yl)pyridazine-3-carboxamide
14. N-(3,5-difluorobenzyl)-6-{[(5-methyl-3-phenylisoxazol-4-yl)methyl]amino}pyridazine-3-carboxamide Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of compounds of formula I may be prepared by one or more of three methods:
(i) by reacting the compound of formula I with the desired acid or base;
(ii) by removing an acid- or base-labile protecting group from a suitable precursor of the compound of formula I or by ring-opening a suitable cyclic precursor, for example, a lactone or lactam, using the desired acid or base; or
(iii) by converting one salt of the compound of formula Ito another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975).

When appropriate to the context, references to compounds of formula I below include references to salts, solvates and complexes thereof and to solvates and complexes of salts thereof.

The compounds of the invention include all polymorphs and crystal habits thereof, prodrugs and isomers thereof (including optical, geometric and tautomeric isomers) as hereinafter defined and isotopically-labeled compounds of formula I.

As indicated, so-called 'pro-drugs' of the compounds of formula I are also within the scope of the invention. Thus certain derivatives of compounds of formula I which may have little or no pharmacological activity themselves can, when administered into or onto the body, be converted into compounds of formula I having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula I with certain moieties known to those skilled in the art as 'pro-moieties' as described, for example, in *Design of Prodrugs* by H. Bundgaard (Elsevier, 1985).

Some examples of prodrugs in accordance with the invention include
(i) where the compound of formula I contains a carboxylic acid functionality (—COOH), an ester thereof, for example, a compound wherein the hydrogen of the carboxylic acid functionality of the compound of formula (I) is replaced by ($C_1$-$C_8$)alkyl;
(ii) where the compound of formula I contains an alcohol functionality (—OH), an ether thereof, for example, a compound wherein the hydrogen of the alcohol functionality of the compound of formula I is replaced by ($C_1$-$C_6$)alkanoyloxymethyl; and (iii) where the compound of formula I contains a primary or secondary amino functionality (—$NH_2$ or —NHR where R≠H), an amide thereof, for example, a compound wherein, as the case may be, one or both hydrogens of the amino functionality of the compound of formula I is/are replaced by ($C_1$-$C_{10}$)alkanoyl.

Further examples of replacement groups in accordance with the foregoing examples and examples of other prodrug types may be found in the aforementioned references.

Moreover, certain compounds of formula I may themselves act as prodrugs of other compounds of formula I.

Also included within the scope of the invention are metabolites of compounds of formula I, that is, compounds formed in vivo upon administration of the drug. Some examples of metabolites in accordance with the invention include (i) where the compound of formula I contains a methyl group, an hydroxymethyl derivative thereof (—$CH_3$—>—$CH_2OH$):
(ii) where the compound of formula I contains an alkoxy group, an hydroxy derivative thereof (—OR—>—OH);
(iii) where the compound of formula I contains a tertiary amino group, a secondary amino derivative thereof (—$NR^1R^2$—>—$NHR^1$ or —$NHR^2$);
(iv) where the compound of formula I contains a secondary amino group, a primary derivative thereof (—$NHR^1$—>—$NH_2$);
(v) where the compound of formula I contains a phenyl moiety, a phenol derivative thereof (-Ph->-PhOH); and
(vi) where the compound of formula I contains an amide group, a carboxylic acid derivative thereof (—$CONH_2$—>COOH).

Compounds of formula I containing one or more asymmetric carbon atoms can exist as two or more stereoisomers. Where a compound of formula I contains an alkenyl or alkenylene group, geometric cis/trans (or Z/E) isomers are possible. Where structural isomers are interconvertible via a low energy barrier, tautomeric isomerism (tautomerism) can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

The present invention includes all pharmaceutically acceptable isotopically-labelled compounds of formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

Compounds of formula I may be prepared by reacting a compound of formula II,

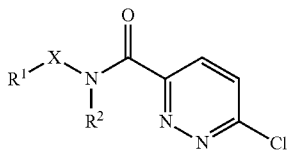
(II)

wherein X, R¹ and R² are as defined above, with an amine of formula III,

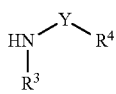
(III)

wherein Y, R³ and R⁴ are as defined above.

Typically the chloropyridazine of formula II is treated with a solution of the amine of formula III in the presence of a base in an organic solvent at an elevated temperature for 48 hours. Preferably, the chloropyridazine of formula II is treated with 3 equivalents of the amine of formula III. Suitable solvents include anhydrous dimethyl sulfoxide. A preferred base is N,N-diisopropylethylamine. A suitable temperature for the reaction is 60° C.

Compounds of formula III are either commercially available or may be prepared according to known synthetic methods.

Compounds of formula II may be prepared by coupling the compound of formula IV,

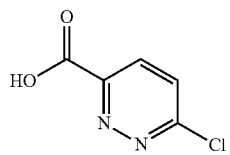
(IV)

with a compound of formula V,

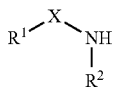
(V)

wherein X, R¹ and R² are as defined above.

Typically the acid of formula IV is activated with reagents like thionyl chloride, oxalyl chloride, 1,1'-carbonyl diimidazole (DCI), 1-propanephosphonic acid cyclic anhydride, 1-hydroxybenzotriazole hydrate, optionally in the presence of a catalyst like N,N-dimethyl formamide, and then the intermediate activated acid is treated with the amine of formula V in an organic solvent at room temperature. Preferably, the compound of formula IV is treated with 1.1 equivalents of DCI in anhydrous N,N-dimethylformamide for 120 minutes, followed by addition of the amine of formula V (1 equivalent) in N,N-dimethyl formamide. Preferably, the reaction is shaken at room temperature for 20 hours.

The compound of formula IV is commercially available, and known in the literature. Compounds of formula V are commercially available, known in the literature, or are available using known techniques.

It will be apparent to those skilled in the art that sensitive functional groups may need to be protected and de-protected during synthesis of a compound of the invention. This may be achieved by conventional techniques, for example as described in 'Protective Groups in Organic Synthesis' by Theorora Greene and Peter Wuts (third edition, 1999, John Wiley and Sons).

The invention further provides a compound of formula I, as defined above, or a pharmaceutically acceptable salt or solvate thereof, for use as a pharmaceutical.

The invention further provides a compound of formula I, as defined above, or a pharmaceutically acceptable salt or solvate thereof, for use in the treatment of a disorder selected from: pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

The invention further provides a compound of formula I, as defined above, or a pharmaceutically acceptable salt or solvate thereof, for use in the treatment of a disorder selected from: cancer (including ovarian cancer, breast cancer and prostate cancer), atherosclerosis, thrombosis, psoriasis, multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, causalgia, and conditions of lower urinary tract dysfunction.

The invention further provides a compound of formula I, as defined above, or a pharmaceutically acceptable salt or solvate thereof, for use in the treatment of fibrotic diseases including pulmonary fibrosis, Cirrhosis, endomyocardial fibrosis, mediastinal fibrosis, myelo fibrosis, retroperitoneal fibrosis, nephrogenic systemic fibrosis, Crohn's disease, Keloid, old myocardial infarction, scleroderma/systemic sclerosis, atherofibrosis and adhesive capsulitis.

The invention further provides a pharmaceutical formulation comprising a compound of formula I, as defined above, or a pharmaceutically acceptable salt or solvate thereof, and a pharmaceutically acceptable adjuvant, diluent or carrier. The pharmaceutical formulation may further comprise one or more additional active agents for the treatment of a disorder mentioned above.

The invention further provides a pharmaceutical kit comprising a compound of formula I, as defined above, or a pharmaceutically acceptable salt or solvate thereof, and one or more additional active agents, as a combined preparation for separate, simultaneous or sequential administration in the treatment of a disorder mentioned above.

The invention further provides a method of treatment of a disorder mentioned above in a mammal (especially a human), comprising administration of a therapeutically effective amount of a compound of formula I, as defined above, or a pharmaceutically acceptable salt or solvate thereof, to a mammal in need of such treatment.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of the invention may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula I, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 to 10,000 μg of the compound of the invention. The overall daily dose will typically be in the range 1 μg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula I in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Examples of additional active agents which may be part of a formulation or pharmaceutical kit according to the present invention, particularly for the treatment of pain or pain-related disorders, include:

a Nav1.7 channel modulator, such as a compound disclosed in WO 2009/012242;

a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);

an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;

a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperid ene-1-carboxamide);

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-di hydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a 5-HT$_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)pro line, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist, such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870; and a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quino lone (ZD-2138), or 2,3,5-trimethyl-6-(3-pyridylmethyl), 1,4-benzoquinone (CV-6504).

Examples of additional active agents which may be part of a formulation or pharmaceutical kit according to the present invention, particularly for the treatment of cancer, include:

- an anti-tumour platinum-based compound such as cisplatin or carboplatin;
- an anti-estrogen or selective estrogen receptor modulator such as tamoxifen, afimoxifene, arzoxifene, bazedoxifene, lasofoxifene or nafoxidene; and
- a tyrosine kinase inhibitor such as afatinib, imatinib, gefitinib, sorafenib, sunitinib, vandetanib, crizotinib or lapatinib.

Dosage

For administration to human patients, the total daily dose of the compounds of the invention is typically in the range 0.5 mg to 3000 mg depending, of course, on the mode of administration. For example, oral administration may require a total daily dose of from 3 mg to 3000 mg, while an intravenous dose may only require from 0.5 mg to 500 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

Biological Activity

The biological activity of the compounds of the invention may be measured using the assay described below.

FS-3 Assay

Autotaxin (ATX) converts Lysophosphatidyl choline (LPC) to Lysophosphatidic acid (LPA) via its Lysophosphodiesterase (lysoPLD) activity. FS-3 is an LPC analogue that is conjugated with both a fluorophore and a quencher. In its native state the quencher interferes with the fluorophore's fluorescence. Once autotaxin cleaves FS-3, the fluorophore becomes liberated from the quencher, resulting in increased fluorescence. Thus increase in fluorescence is a measure of ATX activity. Any compound that inhibits the activity of Autotaxin will show less fluorescence read in presence of FS-3, which could be measured by fluorimetric analysis. See U.S. Pat. No. 7,989,663.

Autotaxin Inhibitor Screening Kits are available from Echelon Biosciences, Logan, Utah, USA [http://echelon-inc.com/, accessed 6 Oct. 2011]. Using the methods of Gierse et al ["A novel autotaxin inhibitor reduces lysophosphatidic acid levels in plasma and the site of inflammation", *Journal of Pharmacology and Experimental Therapeutics*, vol 334(1), 310-317 (2010), see in particular page 312 lines 4-14], the potency of the compounds of the invention as inhibitors of human autotaxin enzyme may be measured (as $IC_{50}$ values).

The FS-3 assay to identify ATX inhibitors was preformed as follows: 3 µl of standard inhibitor (referred to as PF-8380 in Gierse et al above) and test compounds were added to an assay plate. To each assay well, containing test compounds or standard, 24 µl of human Autotaxin enzyme (2 nM) was added. The assay plate was then centrifuged at 1000 rpm for 1 minute and allowed to incubate at 37° C. for 30 minutes. Following the incubation period each plate was read in a fluorescence plate reader (Spectra Max M5: excitation: 494 nm and emission: 520 nm) and $IC_{50}$ values were derived from inhibition of FS-3 fluorescence (as described above).

The invention is illustrated by the following Examples.

All starting materials are available commercially or are described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance traveled by a compound divided by the distance traveled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

The following abbreviations and definitions may be used:
APCI atmospheric pressure chemical ionisation
$CDCl_3$ deuterated chloroform
$CD_3OD$ deuterated methanol
DMSO deuterated dimethyl sulphoxide
δ chemical shift
d Doublet
DAD Diode array detector
ESCI electrospray chemical ionisation
HPLC high pressure liquid chromatography
LRMS low resolution mass spectrum
LCMS Liquid chromatography mass spectrum
M molar
m multiplet
mg milligrams
MHz mega hertz
min minutes
mL millilitres
µL microlitres
mmol milli moles
mol moles
MS mass spectrometry
NMR nuclear magnetic resonance
q quartet
Rt retention time
s singlet
t triplet
TFA trifluoroacetic acid
THF tetrahydrofuran
SFC Supercritrical fluid chromatography Where compounds have been analysed by LCMS a Waters Acquity LCMS system has been used with:
Mass Spectrometer Model: Waters ZQ
Ionization Mode: API-ES
Polarity: Positive
Detectors: UV-Acquity PDA; Varian ELSD (evaporative light scattering detector)
Chromatography System
A: 0.1% formic acid in water
B: 0.1% formic acid in acetonitrile
Column: Acquity CSH C18 50×2.1 mm with 1.7 micron particle size
Gradient: 95-5% A over 1.12 min, 0.43 min hold, 1 mL/min
UV: 210 nm-225 nm PDA
Temperature: 50° C.

EXAMPLES 1 TO 14

The compounds of the Examples set out in Table 1 below were prepared in the two step process shown below using the appropriate amine starting materials.

Step 1:

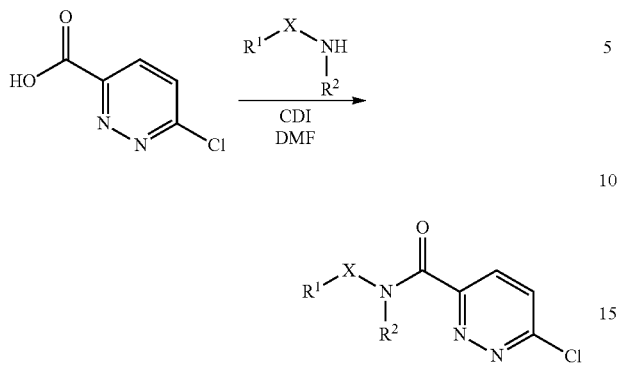

A solution of carbonyldiimidazole (CDI, 165 μL, 1.0 M in N,N-dimethylformamide, 0.165 mmol) was added to a solution of 3-chloropyridazine-6-carboxylic acid (300 μL, 0.5 M in N,N-dimethylformamide, 0.15 mmol) in a vial. The mixture was shaken at room temperature for 2 hours. A solution of the relevant amine (300 μL, 0.5 M in N,N-dimethylformamide, 0.15 mmol) was added and the vials shaken at room temperature for 20 hours. The reaction was evaporated to dryness under vacuum. The residue was partitioned between ethyl acetate (2.5 mL) and water (2 mL). The layers were separated and the organic layer was evaporated and the residue used without further purification in the subsequent step.

Step 2:

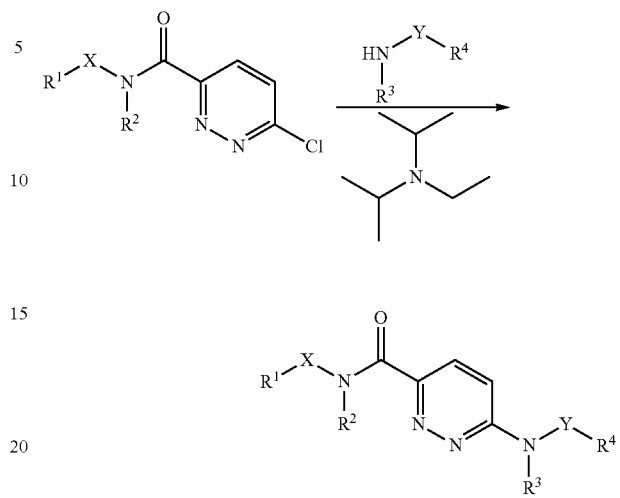

A solution of the relevant amine (900 μL, 0.5 M in dimethylsulfoxide, 0.45 mmol) was added to the residue from Step 1. N,N-diisopropyethylamine (60 μL, 2.3 equivalents) was added and the reaction mixture shaken and heated at 60° C. for 48 hours. Dimethylsulfoxide (0.6 mL) was added and the reaction mixture was purified by HPLC to afford the title compounds.

TABLE 1

| Example No. | Structure/Name | LCMS retention time | LCMS mass detected |
|---|---|---|---|
| 1 | N-(2,5-difluorobenzyl)-6-{[3-hydroxy-1-(4-methoxyphenyl)propyl]amino}pyridazine-3-carboxamide | 0.53 mins | 429 (MH+) |
| 2 | N-(3,5-difluorobenzyl)-6-{[3-hydroxy-1-(4-methoxyphenyl)propyl]amino}pyridazine-3-carboxamide | 0.53 mins | 429 (MH+) |

TABLE 1-continued

| Example No. | Structure/Name | LCMS retention time | LCMS mass detected |
|---|---|---|---|
| 3 | 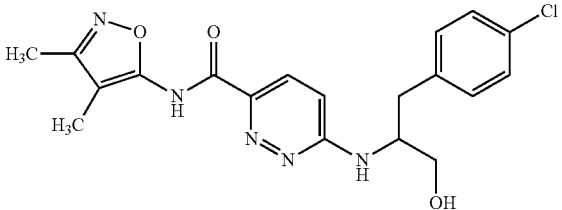<br>6-{[1-(4-chlorobenzyl)-2-hydroxyethyl]amino}-N-(3,4-dimethylisoxazol-5-yl)pyridazine-3-carboxamide | 0.55 mins | 402 (MH+) |
| 4 | 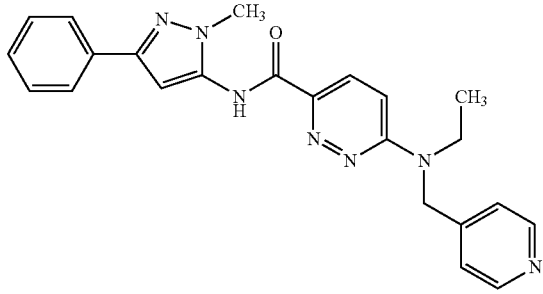<br>6-[ethyl(pyridin-4-ylmethyl)amino]-N-(1-methyl-3-phenyl-1H-pyrazol-5-yl)pyridazine-3-carboxamide | 0.49 mins | 414 (MH+) |
| 5 | 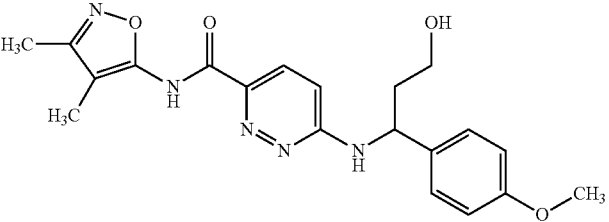<br>N-(3,4-dimethylisoxazol-5-yl)-6-{[3-hydroxy-1-(4-methoxyphenyl)propyl]amino}pyridazine-3-carboxamide | 0.47 mins | 398 (MH+) |
| 6 | 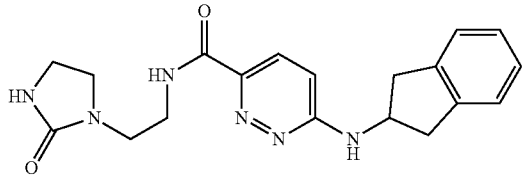<br>6-(2,3-dihydro-1H-inden-2-ylamino)-N-[2-(2-oxo-imidazolidin-1-yl)ethyl]pyridazine-3-carboxamide | 0.39 mins | 367 (MH+) |

TABLE 1-continued

| Example No. | Structure/Name | LCMS retention time | LCMS mass detected |
|---|---|---|---|
| 7 | 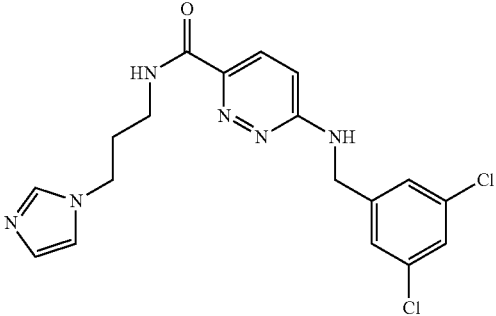<br>6-[(3,5-dichlorobenzyl)amino]-N-[3-(1H-imidazol-1-yl)propyl]pyridazine-3-carboxamide | 0.49 mins | 405 (MH+) |
| 8 | 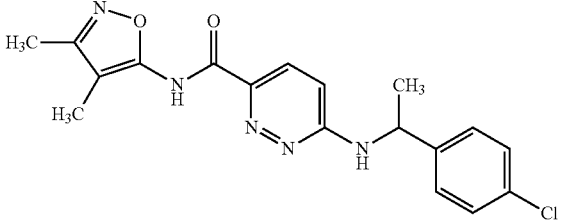<br>6-{[1-(4-chlorophenyl)ethyl]amino}-N-(3,4-dimethylisoxazol-5-yl)pyridazine-3-carboxamide | 0.64 mins | 372 (MH+) |
| 9 | 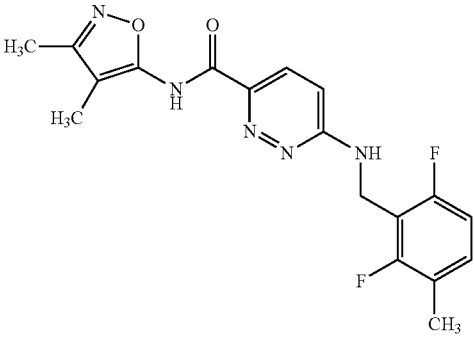<br>6-[(2,6-difluoro-3-methylbenzyl)amino]-N-(3,4-dimethylisoxazol-5-yl)pyridazine-3-carboxamide | 0.61 mins | 374 (MH+) |
| 10 | 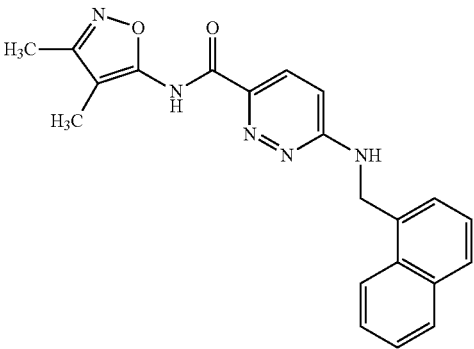<br>N-(3,4-dimethylisoxazol-5-yl)-6-[(1-napthylmethyl)-amino]pyridazine-3-carboxamide | 0.66 mins | 374 (MH+) |

TABLE 1-continued

| Example No. | Structure/Name | LCMS retention time | LCMS mass detected |
|---|---|---|---|
| 11 | 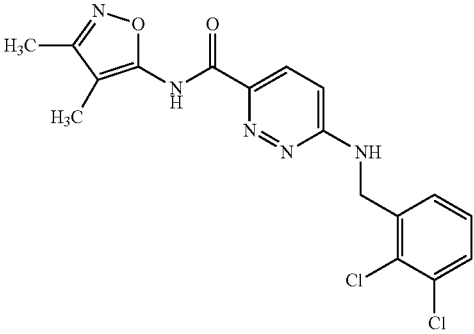<br>6-[(2,3-dichlorobenzyl)amino]-N-(3,4-dimethyl-isoxazol-5-yl)pyridazine-3-carboxamide | 0.63 mins | 392 (MH+) |
| 12 | 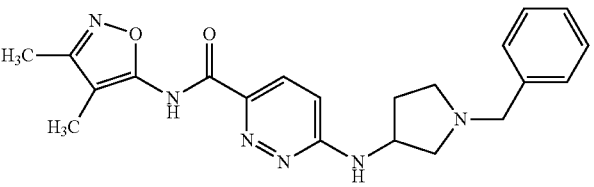<br>6-[(1-benzylpyrrolidin-3-yl)amino]-N-(3,4-dimethyl-isoxazol-5-yl)pyridazine-3-carboxamide | 0.43 mins | 393 (MH+) |
| 13 | 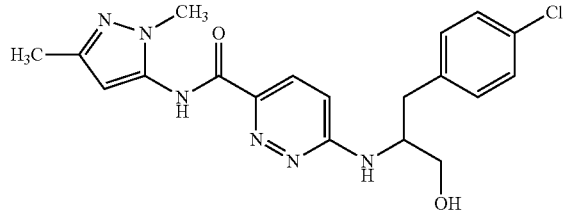<br>6-{[1-(4-chlorobenzyl)-2-hydroxyethyl]amino}-N-(1,3-dimethyl-1H-pyrazol-5-yl)pyridazine-3-carboxamide | 0.49 mins | 401 (MH+) |
| 14 | 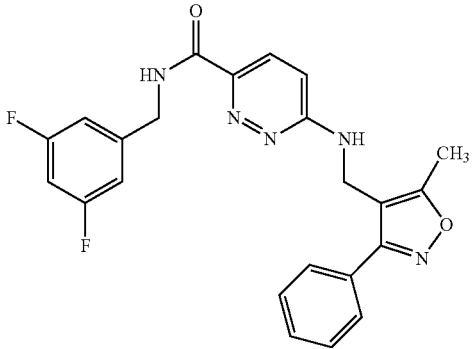<br>N-(3,5-difluorobenzyl)-6-{[(5-methyl-3-phenyl-isoxazol-4-yl)methyl]amino}pyridazine-3-carboxamide | 0.65 mins | 436 (MH+) |

EXAMPLE 15

The compounds of the examples were tested in the Autotaxin FS3 assay described above, with the following results:

| Example No. | IC$_{50}$ (nM) |
|---|---|
| 1 | 14.0 (3.53-55.7 n = 2) |
| 2 | 24.9 (8.60-72.1 n = 4) |
| 3 | 37.6 (33.4-42.5 n = 2) |
| 4 | 65.2 (8.26-515 n = 2) |
| 5 | 69.5 (69.2-69.9 n = 2) |
| 6 | 73.8 (23.7-230 n = 2) |
| 7 | 89.2 (88.1-90.4 n = 2) |
| 8 | 100 (78.5-128 n = 2) |
| 9 | 103 (15.9-670 n = 2) |
| 10 | 114 (33.4-388 n = 2) |
| 11 | 248 (1.54-40100 n = 2) |
| 12 | 357 (56.4-2260 n = 2) |
| 13 | 507 (85.7-3000 n = 2) |
| 14 | 646 (597-699 n = 4) |

The invention claimed is:

1. A compound of formula (I),

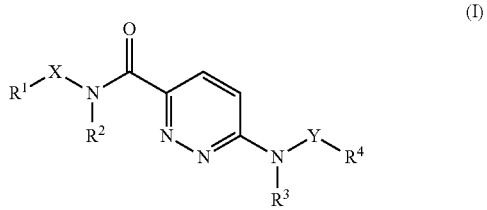

wherein:
- $R^1$ represents a cyclic group selected from phenyl, heteroaryl$^1$, heterocyclyl$^1$ and $C_{3-6}$ cycloalkyl;
- wherein each cyclic group is optionally substituted with from 1 to 3 substituents selected from halo, $C_{1-6}$ alkyl optionally substituted with 1-3 halogen atoms, phenyl, $C_{1-6}$ alkoxy optionally substituted with 1-3 halogen atoms, cyano, heteroaryl$^{1a}$ and heterocycly$^{1a}$; and
- wherein each cyclic group is optionally fused to a benzene ring or a 5- or 6-membered heteroaromatic or heterocyclic ring each containing from 1 to 3 heteroatoms selected from N, O and S; and when the group is substituted the substitution may occur anywhere on the optionally fused ring system as a whole; and
- wherein heterocyclyl$^1$ and heterocyclyl$^{1a}$ may additionally be substituted with =O;
- X represents a bond or $C_{1-6}$ alkylene;
- $R^2$ represents H or $C_{1-6}$ alkyl;
- $R^3$ represents H or $C_{1-6}$ alkyl;
- Y represents $CH(CH_2CH_2OH)$;
- $R^4$ represents a cyclic group selected from phenyl, heteroaryl$^4$, heterocyclyl$^4$ and $C_{3-6}$ cycloalkyl;
- wherein each cyclic group is optionally substituted with from 1 to 3 substituents selected from halo, $C_{1-6}$ alkyl optionally substituted with 1-3 halogen atoms, phenyl, $C_{1-6}$ alkyl substituted with phenyl, $C_{1-6}$ alkoxy optionally substituted with 1-3 halogen atoms, cyano, heteroaryl$^{4a}$ and heterocyclyl$^{4a}$; and
- wherein each cyclic group is optionally fused to benzene ring or a 5- or 6-membered heteroaromatic or heterocyclic ring each containing from 1 to 3 heteroatoms selected from N, O and S; and when the group is substituted the substitution may occur anywhere on the optionally fused ring system as a whole; and
- wherein heterocyclyl$^4$ and heterocyclyl$^{4a}$ may additionally be substituted with =O;
- heteroaryl$^1$, heteroaryl$^{1a}$, heteroaryl$^4$ and heteroaryl$^{4a}$ independently represent a 5- or 6-membered heteroaryl group containing from 1 to 3 heteroatoms selected from N, O and S; and
- heterocyclyl$^1$, heterocyclyl$^{1a}$, heterocyclyl$^4$ and heterocyclyl$^{4a}$ independently represent a 5- or 6-membered heterocyclyl group containing from 1 to 3 heteroatoms selected from N, O and S; and
- pharmaceutically acceptable salts thereof.

2. The compound as claimed in claim 1, wherein $R^1$ represents phenyl substituted by one or two fluorine atoms, and pharmaceutically acceptable salts thereof.

3. The compound as claimed in claim 1, wherein X represents $CH_2$ or a bond, and pharmaceutically acceptable salts thereof.

4. The compound as claimed in claim 1, wherein $R^2$ represents H, and pharmaceutically acceptable salts thereof.

5. The compound as claimed in claim 1, wherein $R^3$ represents H, and pharmaceutically acceptable salts thereof.

6. The compound as claimed in claim 1, wherein $R^4$ represents phenyl substituted in the 4-position by methoxy, a halogen atom, methyl or ethyl, and pharmaceutically acceptable salts thereof.

7. A pharmaceutical formulation comprising the compound of formula (I), as claimed in claim 1, or a pharmaceutically acceptable salt thereof, and a pharmaceutically acceptable adjuvant, diluent or carrier.

8. The pharmaceutical formulation as claimed in claim 7, further comprising one or more additional pain relieving agents.

9. A pharmaceutical kit comprising the compound of formula (I), as claimed in claim 1, or a pharmaceutically acceptable salt thereof, and one or more additional pain relieving agents.

10. The pharmaceutical kit as claimed in claim 9, wherein the pain relieving agent relieves a pain selected from the group consisting of acute pain, chronic pain, neuropathic pain, inflammatory pain, visceral pain, nociceptive pain and osteoarthritis.

11. The pharmaceutical kit as claimed in claim 10, wherein the nociceptive pain is selected from the group consisting of post-surgical pain and mixed pain involving the the viscera, gastrointestinal tract, cranial structure, spine, musculoskeletal system, urogenital system, cardiovascular system or central nervous system.

12. The pharmaceutical kit as claimed in claim 11, wherein the mixed pain is selected from the group consisting of cancer pain, back pain, orofacial pain, pelvic pain, peripheral neuropathic pain and pain associated with a disease or disorder selected from the group consisting of atherosclerosis, thrombosis, psoriasis, multiple sclerosis, irritable bowel syndrome, rheumatoid arthritis, dysmenorrhea, cystitis, pancreatitis, migraine, cluster headache, tension headache, diabetic neuropathy, sciatica, fibromyalgia, causalgia, lower urinary tract dysfunction, a neurodegenerative disorder, a neuropathological disorder, a functional bowel disorder and an inflammatory bowel disease.

13. A method for inhibiting autotaxin activity in a mammal suffering from pain, comprising administering to said mammal a therapeutically effective amount of the compound of formula (I), as claimed in claim 1, or a pharmaceutically acceptable salt thereof.

14. The method as claimed in claim 13, wherein the pain is selected from the group consisting of acute pain, chronic pain, neuropathic pain, inflammatory pain, visceral pain, nociceptive pain and osteoarthritis.

15. The method as claimed in claim 14, wherein the nociceptive pain is selected from the group consisting of post-surgical pain and mixed pain involving the the viscera, gastrointestinal tract, cranial structure, spine, musculoskeletal system, urogenital system, cardiovascular system or central nervous system.

16. The method as claimed in claim 15, wherein the mixed pain is selected from the group consisting of cancer pain, back pain, orofacial pain, pelvic pain, peripheral neuropathic pain and pain associated with a disease or disorder selected from the group consisting of atherosclerosis, thrombosis, psoriasis, multiple sclerosis, irritable bowel syndrome, rheumatoid arthritis, dysmenorrhea, cystitis, pancreatitis, migraine, cluster headache, tension headache, diabetic neuropathy, sciatica, fibromyalgia, causalgia, lower urinary tract dysfunction, a neurodegenerative disorder, a neuropathological disorder, a functional bowel disorder and an inflammatory bowel disease.

17. A method for inhibiting autotaxin activity in a mammal suffering from a fibrotic disease, comprising administering to said mammal a therapeutically effective amount of the compound of formula (I), as claimed in claim 1, or a pharmaceutically acceptable salt thereof.

18. The method as claimed in claim 17, wherein the fibrotic disease is selected from the group consisting of pulmonary fibrosis, cirrhosis, endomyocardial fibrosis, mediastinal fibrosis, myelofibrosis, retroperitoneal fibrosis, nephrogenic systemic fibrosis, Crohn's disease, keloid, old myocardial infarction, systemic sclerosis, atherofibrosis and adhesive capsulitis.

19. A method for inhibiting autotaxin activity in a mammal suffering from pain, fibrosis, osteoarthritis, rheumatoid arthritis, multiple sclerosis, atherosclerosis, thrombosis, psoriasis, neuropathy, cancer or an inflammatory condition, comprising administering to said mammal a therapeutically effective amount of the compound of formula (I), as claimed in claim 1, or a pharmaceutically acceptable salt thereof.

20. A process for the production of the compound of formula (I), as claimed in claim 1, which comprises reacting a compound of formula (II),

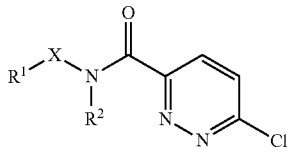

(II)

with an amine of formula (III),

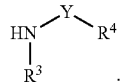

(III)

* * * * *